(12) United States Patent
Putz (10) Patent No.: US 7,322,954 B2
(45) Date of Patent: Jan. 29, 2008

(54) CATHETER ASSEMBLY FOR INTRACRANIAL TREATMENT USING DUAL LUMENS

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 11/262,375

(22) Filed: Oct. 28, 2005

(65) Prior Publication Data

US 2006/0079830 A1   Apr. 13, 2006

Related U.S. Application Data

(63) Continuation-in-part of application No. 10/423,587, filed on Apr. 25, 2003, now Pat. No. 7,241,283.

(51) Int. Cl.
*A61M 3/00* (2006.01)

(52) U.S. Cl. .................... 604/43; 604/164.09

(58) Field of Classification Search ........... 604/160, 604/161, 164.01–164.11, 166.01, 170.01, 604/170.02, 167.01, 167.02, 167.06, 158, 604/43–45, 264

See application file for complete search history.

(56) References Cited

U.S. PATENT DOCUMENTS

| | | | |
|---|---|---|---|
| 4,346,709 A | 8/1982 | Schmitt | |
| 4,471,779 A | 9/1984 | Antoshkiw et al. | |
| 4,613,324 A | 9/1986 | Ghajar | |
| 4,685,901 A | 8/1987 | Parks | |
| 4,777,951 A | 10/1988 | Cribier et al. | |
| 4,798,586 A | 1/1989 | Stevens | |
| 4,848,344 A * | 7/1989 | Sos et al. ............ | 606/194 |
| 4,892,538 A | 1/1990 | Aebischer et al. | |
| 4,921,478 A | 5/1990 | Solano et al. | |
| 5,009,636 A * | 4/1991 | Wortley et al. ........... | 604/43 |
| 5,033,998 A | 7/1991 | Corday et al. | |
| 5,041,090 A | 8/1991 | Scheglov et al. | |
| 5,064,654 A | 11/1991 | Berner et al. | |
| 5,081,990 A | 1/1992 | Deletis | |
| 5,087,244 A | 2/1992 | Wolinsky et al. | |
| 5,108,364 A * | 4/1992 | Takezawa et al. .......... | 604/43 |
| 5,119,832 A | 6/1992 | Xavier | |
| 5,154,179 A * | 10/1992 | Ratner ................... | 600/420 |
| 5,191,898 A | 3/1993 | Millar | |
| 5,300,022 A * | 4/1994 | Klapper et al. ........... | 604/35 |

(Continued)

*Primary Examiner*—Nicholas Lucchesi
*Assistant Examiner*—Theodore J. Stigell
(74) *Attorney, Agent, or Firm*—Jansson Shupe & Munger Ltd.

(57) ABSTRACT

A catheter assembly is provided for intracranial treatment having outer and inner catheters. The outer catheter has a first lumen communicating between a first opening and at least one aperture and a second lumen in communication with a second opening. The first and second openings are distal to the proximal portion of the outer catheter. The inner catheter, preferably a micro-dialysis catheter, is sized to be received within the first lumen and includes at least one passageway in communication with at least one port for transfer of a fluid with a tissue region in the brain of the patient. The assembly preferably also includes a stylet sized to be received within the second lumen to provide rigidity to the outer catheter for its precise positioning within the brain. The outer catheter can include an element that is preferably a contact for monitoring brain activity. A method of transferring a fluid with a brain tissue region is also disclosed.

31 Claims, 6 Drawing Sheets

U.S. PATENT DOCUMENTS

| | | |
|---|---|---|
| 5,330,768 A | 7/1994 | Park et al. |
| 5,423,877 A | 6/1995 | Mackey |
| 5,458,631 A | 10/1995 | Xavier |
| 5,505,698 A | 4/1996 | Booth et al. |
| 5,662,607 A | 9/1997 | Booth et al. |
| 5,676,655 A | 10/1997 | Howard et al. |
| 5,697,975 A | 12/1997 | Howard et al. |
| 5,711,316 A | 1/1998 | Elsberry et al. |
| 5,713,858 A | 2/1998 | Heruth et al. |
| 5,728,066 A | 3/1998 | Daneshvar |
| 5,782,798 A | 7/1998 | Rise |
| 5,792,100 A | 8/1998 | Shantha |
| 5,792,110 A | 8/1998 | Cunningham |
| 5,795,331 A | 8/1998 | Cragg et al. |
| 5,807,328 A | 9/1998 | Briscoe |
| 5,810,767 A | 9/1998 | Klein |
| 5,843,022 A | 12/1998 | Willard et al. |
| 5,868,704 A | 2/1999 | Campbell et al. |
| 5,975,085 A | 11/1999 | Rise |
| 6,017,323 A | 1/2000 | Chee |
| 6,030,358 A * | 2/2000 | Odland ............... 604/27 |
| 6,041,252 A | 3/2000 | Walker et al. |
| 6,096,021 A | 8/2000 | Helm et al. |
| 6,120,477 A | 9/2000 | Campbell et al. |
| 6,203,526 B1 | 3/2001 | McBeth et al. |
| 6,210,346 B1 * | 4/2001 | Hall et al. ............ 600/561 |
| 6,251,115 B1 | 6/2001 | Williams et al. |
| 6,263,225 B1 | 7/2001 | Howard, III |
| 6,264,633 B1 | 7/2001 | Knorig |
| 6,283,951 B1 * | 9/2001 | Flaherty et al. ....... 604/529 |
| 6,510,347 B2 | 1/2003 | Borkan |
| 6,527,782 B2 | 3/2003 | Hogg et al. |
| 6,629,990 B2 | 10/2003 | Putz et al. |
| 6,656,152 B2 | 12/2003 | Putz |
| 6,733,474 B2 | 5/2004 | Kusleika |
| 6,773,447 B2 | 8/2004 | Laguna |
| 6,832,115 B2 | 12/2004 | Borkan |
| 6,887,229 B1 | 5/2005 | Kurth |

* cited by examiner

CATHETER ASSEMBLY FOR INTRACRANIAL TREATMENT USING DUAL LUMENS

RELATED APPLICATION

This application is a continuation-in-part of U.S. patent application Ser. No. 10/423,587, filed on Apr. 25, 2003, now U.S. Pat. No. 7,241,283.

FIELD OF INVENTION

The present invention relates to catheter assemblies for intracranial treatment and, in particular, to catheter assemblies for the intracranial transfer of fluids.

BACKGROUND OF THE INVENTION

Movement disorders such as epilepsy and Parkinson's disease have been estimated to affect some 1-2% of the developed world's population and up to 10% of people in underdeveloped countries. Currently, approximately 75% of those who suffer from movement disorders are responsive in some degree to drugs.

Electrical stimulation has also been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

In treatment, electrical stimulation has been used with the recording and analysis of changes in brain activity to predict the occurrence of epileptic seizures. The time of onset of such seizures is often predictable by neural discharge monitoring, even when the exact causal nature of precipitating dysfunction is not understood. Electrodes have been used to obtain signals representative of current brain activity along with a signal processor for continuous monitoring and analysis of these electrical signals in order to identify important changes or the appearance of precursors predictive of an impending change.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

Improved intracranial monitoring devices have been shown to facilitate treatments of movement disorders. Monitoring is typically performed by instruments which are inserted into the brain at different locations or along different tracks. Other systems employ a single device which must be removed and reinserted to provide for delivery of multiple drugs or use of different electrical devices.

Since the introduction of probes or other similar devices into the brain is common in many surgical procedures today, there are a variety of probes available. Such probes typically include ports for drug delivery or electrical, chemical, electrochemical, temperature and/or pressure contacts which enable the observation and analysis of the brain state or contacts providing stimulation. These ports and contacts must typically be positioned at specific points or regions in the brain.

Probes used in intracranial penetration are typically fabricated so that their introduction to the brain is as minimally traumatic as possible. In addition to being minimally traumatic during insertion, certain inserted probes must also be able to remain implanted without causing injury through unintended movement. In some uses, a probe may be implanted and remain in the patient's brain for weeks or longer. Changes in the positioning of the probe often occur during placement or during such extended periods. Therefore, the probe must be capable of precise placement and as bio-compatible as possible. In response to these requirements, state of the art intracranial probes are typically thin, flexible pieces with smooth surfaces to minimize the amount of brain tissue contacted and to minimize damage to contacted brain tissue.

While such thin, flexible probes are sufficiently bio-compatible, they are delicate and often difficult to insert along specific trajectories or lines of insertion. During typical implantation, a surgeon feeds the probe into the brain through an aperture in the skull. In this process, the surgeon has very little control over the distal end of the probe. In order to provide more rigidity to the probe to overcome this problem, a removable stylet may be inserted into the probe before implantation. Still, veering from the intended line of insertion is not altogether prevented by introduction of a stylet to the probe.

There is a continuing significant need in the field of intracranial treatment, particularly with insertion of probes into the interior of the brain, for improvements in accuracy of insertion and avoidance of injury, while retaining efficiency and ease of use.

In addition, there is a need in the field of intracranial treatment to minimize the invasiveness of intracranial treatment and to reduce the number of instruments which penetrate brain tissue or the number of times a single instrument must penetrate brain tissue.

Furthermore, there is a need in the field of intracranial treatment to provide the ability to precisely locate the position of a probe during insertion to ensure proper positioning.

OBJECTS OF THE INVENTION

It is a primary object of the invention to provide an improved intracranial catheter assembly that overcomes some of the problems and shortcomings of the prior art.

Another object of the invention is to provide a novel catheter assembly which is simple in structure and operation in order to facilitate intracranial procedures.

Another object of the invention is to provide an exceptional catheter assembly which allows for the precise insertion of inner catheters for drug delivery or for receiving cerebral spinal fluid while avoiding extensive trauma to and scarring of brain tissue.

Another object of the invention is to provide a desirable catheter assembly having an outer catheter with dual lumens such that an inner catheter can be received and guided through a lumen having a shorter length than that of the lumen into which a stylet is inserted for proper positioning of the outer catheter within the brain.

Another object of the invention is to provide an excellent catheter assembly having an outer catheter that includes contacts for stimulation and/or for monitoring the brain and that receives and guides a drug delivery catheter to the targeted brain tissue for drug delivery.

Another object of the invention is to provide an improved catheter assembly having an outer catheter that includes contacts for stimulation and/or monitoring the brain and that receives and guides a cerebral spinal fluid recovery catheter to the targeted brain tissue for sampling cerebral spinal fluid through a dialysis membrane.

Another object of the invention is to provide a novel catheter assembly having an outer catheter that receives and guides one of a plurality of inner catheters for delivering or removing fluid from the targeted brain tissue and remains in position when the inner catheter is removed, allowing for repeated insertions of different inner catheters without extended contact with brain tissue during insertion.

Yet another object of the invention is to provide a method of safely inserting, through use of an outer catheter, an inner catheter with dual passageways into a patient's brain to provide for delivery of a liquid agent and for withdrawal of cerebral spinal fluid.

SUMMARY OF THE INVENTION

The invention is for a catheter assembly to provide intracranial treatment of a patient. The catheter assembly comprises both outer and inner catheters. The outer catheter has a first lumen communicating between a first opening and at least one aperture and a second lumen in communication with a second opening. The first and second openings are distal to the proximal portion of the outer catheter. The inner catheter is sized to be received within the first lumen and includes at least one passageway in communication with at least one port for transfer of a fluid with a tissue region in the brain of the patient.

In certain preferred embodiments, the catheter assembly also includes a rigid stylet and a plug member. The stylet is sized to be received within the second lumen to aid in the insertion of the outer catheter into the brain. The plug member is adapted to snugly engage within the second opening so that it can close off the second lumen after the outer catheter is inserted and the stylet is removed. More preferred is where the second lumen is also in communication with the aperture.

In another desirable embodiment, the outer catheter has a closed distal end and the aperture is spaced from the distal end along the exterior of the outer catheter. Also desirable is where the outer catheter has first and second apertures in communication with the first lumen that are spaced axially along the exterior of the catheter. A most desirable embodiment finds the first and second apertures spaced radially about the axis of the catheter along its exterior.

One highly preferred embodiment finds the inner catheter to be a micro-dialysis catheter having a dialysis membrane at its port. The membrane is adapted to receive cerebral spinal fluid through the aperture. More desirable is where the inner catheter includes first and second passageways communicating with the port so that a liquid agent can be transferred to a tissue region through the first passageway and cerebral spinal fluid can be withdrawn through a dialysis membrane in the second passageway.

Most preferred is an embodiment where the aperture is at the distal end of the outer catheter. In such embodiments, it is highly desirable that the inner catheter be chosen from a plurality of inner catheters where each inner catheter has a different length to allow the catheter to transfer a fluid with a selected tissue region of the brain. Each inner catheter is sized to extend through the aperture when inserted into the outer catheter. More desirable is where first and second inner catheters are chosen from this plurality of inner catheters, each inner catheter preferably being a micro-dialysis catheter. In such embodiments, the first inner catheter has a length that allows it to transfer the fluid with a selected first tissue region and the second inner catheter has a second length to allow it to transfer the fluid with a selected second tissue region, the second length being greater than the first length so that the second tissue region can be selected at a greater distance away from the aperture than the first tissue region.

In other embodiments that are found desirable, the outer catheter is flexibly deformable such that it can be selectively configured to form a bend proximal to one opening so that it positions that opening in axial alignment with the catheter's distal end. Also preferred is where the outer catheter includes a distal portion having at least one element. A most desirable case of this embodiment finds that the element is a contact that monitors brain activity, preferable electrical activity. More desirable is where the contact is a micro-contact. Highly desirable embodiments find the element to be a location marker for identifying the position of the outer catheter when it is inserted within the brain.

One preferred embodiment finds the outer catheter having at least two elements that are spaced along the distal portion of the catheter. Highly desirable is where the proximal portion of the outer catheter includes a proximal-contact that is conductively connected with an element. The term "conductively connected" is meant to include a connection via a lead in the form of a wire or fiber-optic bundle for the transmission of electrical and/or optical signals.

Another aspect of this invention finds a method for transferring a fluid with a tissue region in the brain. The method includes the steps of (1) inserting a distal portion of an outer catheter having first and second lumens into a targeted area of the brain of a patient, the first lumen being in communication with a first opening and an aperture, the second lumen being in communication with a second opening, and the first and second openings being distal to the proximal portion of the catheter; (2) inserting an inner catheter into the first lumen at the first opening to guide it to the tissue region within the targeted area, the inner catheter having a passageway in communication with a port; and (3) transferring the fluid with the tissue region through the aperture of the outer catheter and the port of the inner catheter.

In a preferred embodiment, a rigid stylet is positioned within the second lumen during the step of inserting the outer catheter into the brain and the method includes the steps of removing the stylet and positioning a plug member within the second lumen. More preferred is where the outer catheter is flexibly deformable and the method has the added step of bending the outer catheter proximal to its openings to position the second opening in axial alignment with the catheter's distal end.

A most desirable embodiment finds the outer catheter having a closed distal end and the aperture spaced from the distal end along the catheter's exterior. Highly desirable is where the inner catheter is a micro-dialysis catheter having a dialysis membrane secured to its port. In such cases, the membrane is adapted to receive cerebral spinal fluid and the transferring step includes withdrawing cerebral spinal fluid from the tissue region through the membrane. The micro-dialysis catheter preferably includes a tapered fitting at its proximal end so that a pumping instrument can be connected to the fitting during the withdrawing step. Cerebral spinal fluid can thereby be withdrawn through the passageway for transfer to and analysis at an external location.

Another preferred embodiment is where the aperture is at the distal end of the outer catheter. In these embodiments, it is desirable that the inner catheter be a micro-dialysis catheter having a dialysis membrane and the method further comprises the step of extending the micro-dialysis catheter through the aperture into the tissue region for withdrawing cerebral spinal fluid from the region through the membrane.

In such embodiments, it is also highly desirable that the inner catheter be chosen from a plurality of inner catheters having different lengths so that it has the length for reaching the selected tissue region and the step of inserting the inner catheter includes extending the inner catheter through the aperture into this tissue region. More preferable is where each inner catheter of this plurality is a micro-dialysis catheter having a dialysis membrane so that the transferring step also includes withdrawing cerebral spinal fluid from the tissue region through the membrane.

One desirable embodiment finds the outer catheter having at least one element mounted proximal to its distal end upon the exterior surface of its distal portion. Most desirable is where the element is a contact and the method includes the step of monitoring brain activity, preferably electrical activity, within the tissue region utilizing the contact. More desirable is where the element is a contact and the method adds the step of providing electrical stimulation to the tissue region utilizing this contact. Highly desirable cases find the proximal portion of the outer catheter having at least one proximal-contact that is conductively connected with the element.

Another aspect of this invention is directed to a depth probe for intracranial treatment of a patient. The depth probe includes a body having first and second openings and at least one aperture, the openings being distal to the proximal portion of the body. The body defines a first lumen that communicates with the first opening and the aperture and is sized to receive an inner catheter adapted to transfer fluids within a tissue region of the brain. The body also defines a second lumen that is in communication with the second opening where the second lumen is sized to receive a stylet adapted to facilitate insertion of the depth probe into the selected tissue region.

Certain preferred embodiments find that the second opening is sized to receive and snugly engage a plug member for closing off the second lumen. More preferred is where the body has first and second apertures in communication with the first lumen and the apertures are spaced axially along the exterior of the body. Highly preferred is where the body has first and second apertures in communication with the first lumen and the apertures are spaced radially about the axis of the body along its exterior.

In another desirable embodiment, the body is flexibly deformable in a manner where it can be selectively configured to form a bend proximal to one opening so as to position that opening of the body in axial alignment with its distal end.

A preferred embodiment finds the distal portion of the body having at least one element and the openings being proximal to this portion. Much preferred is where the element is a contact that monitors brain activity within the tissue region. More desirable is where the element is a micro-contact. Certain highly preferred cases have the element be a location marker to identify the position of the distal portion when the probe is inserted within the brain. Also highly desirable is where there are at least two elements spaced along the distal portion.

DETAILED DESCRIPTION OF PREFERRED EMBODIMENTS

Figure 1:
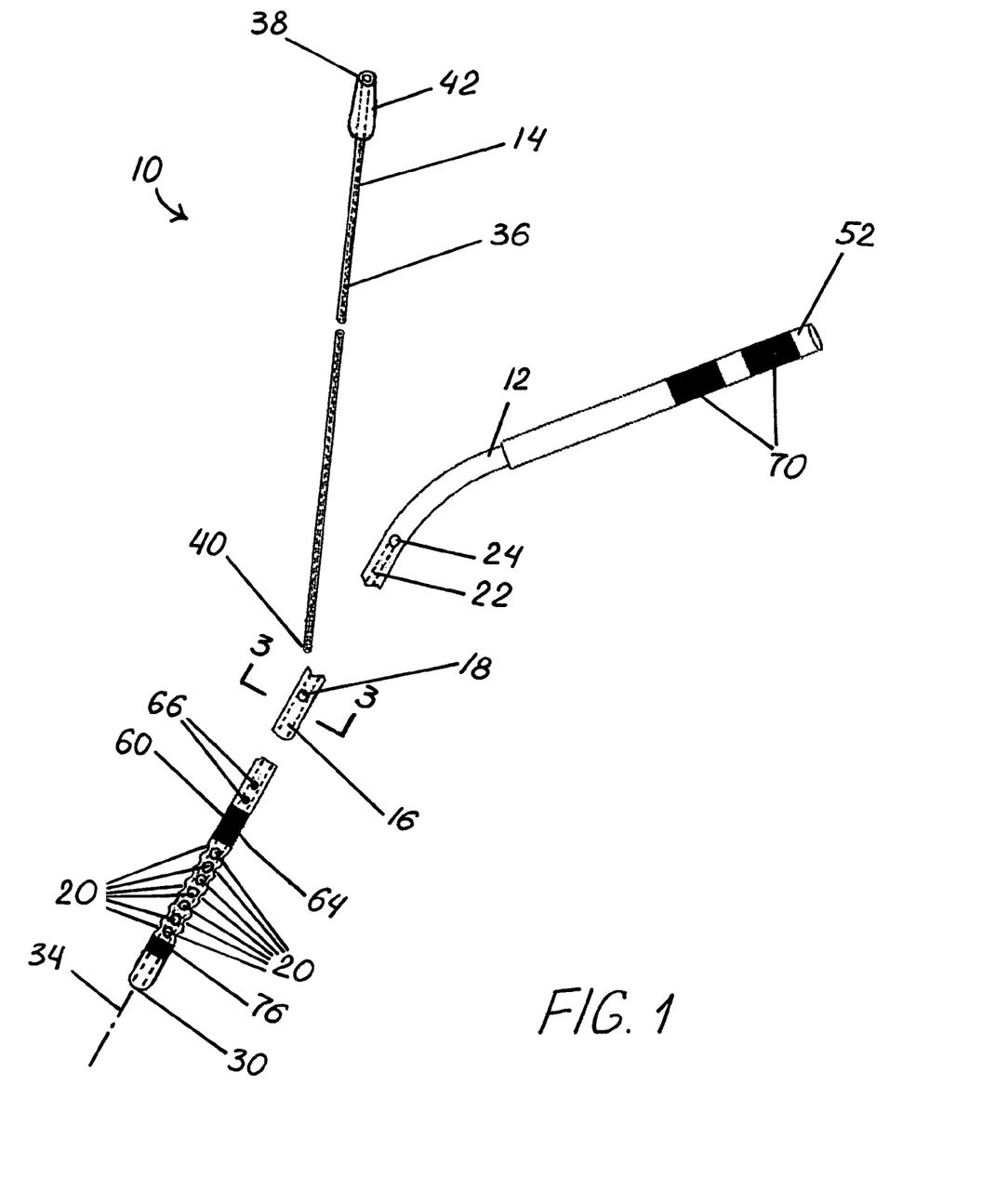
FIG. 1 is a perspective view of a preferred catheter assembly in accordance with this invention with cut-away sections to reveal and dashed lines to represent otherwise unseen internal features.

The figures illustrate preferred embodiments of an improved catheter assembly for intracranial treatment of a patient in accordance with this invention. FIG. 1 is a perspective view of catheter assembly 10 comprising of outer catheter 12 and inner catheter 14. Outer catheter 12 and inner catheter 14 cooperate to transfer fluids between a tissue region in the patient's brain and an external receptacle or device.

Figure 3:
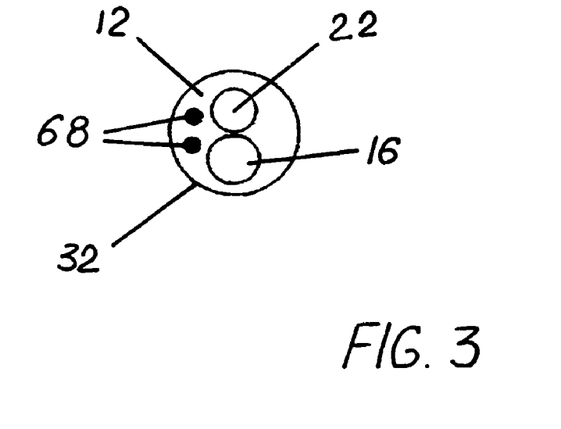
FIG. 3 is a cross-section view taken substantially along the line 3-3 of FIG. 1.

Outer catheter 12 is an elongated, tubular structure having a diameter preferably between about 0.6 and 3.0 millimeters, most preferably about 1.0 millimeter, and is comprised of flexible, bio-compatible materials such as polyurethane, silicone, or polyimide. As illustrated in FIGS. 1 and 3, outer catheter 12 is provided with first lumen 16 extending from first opening 18 and in communication with apertures 20. First lumen 16 is sized to receive inner catheter 14, i.e., first lumen 16 has a diameter slightly greater than the outside diameter of inner catheter 14. Outer catheter 12 is also provided with second lumen 22 extending from second opening 24. Each lumen is a tubular channel extending for some length within outer catheter 12.

Figure 2:
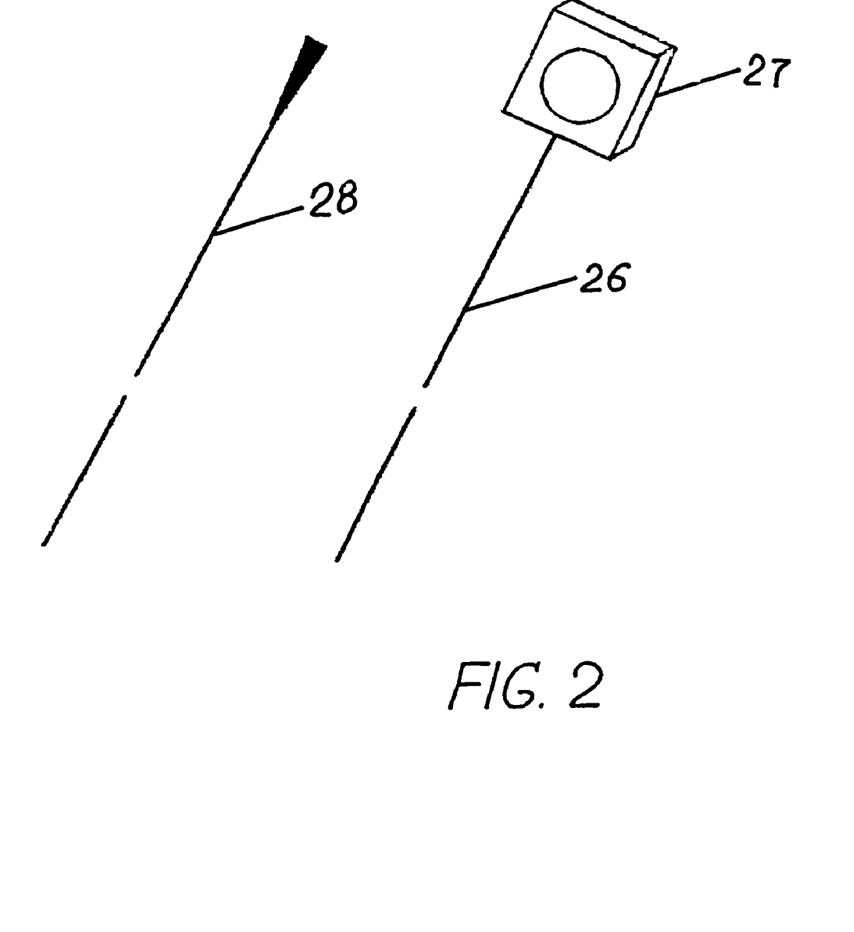
FIG. 2 is a perspective view of a preferred stylet and plug member in accordance with this invention with cut-away sections.

Catheter assembly 10 preferably includes stylet 26 which is shown in FIG. 2. Stylet 26 has a diameter or thickness slightly smaller than the diameter of second lumen 22 so that stylet 26 is receivable within second lumen 22 for use during insertion of outer catheter 12 into the brain. Stylet 26 is rigid to allow for precise positioning of outer catheter 12 inside the brain. Stylet 26 is preferably formed from stainless steel, tungsten or other non-ferrous MRI safe/compatible alloys. In certain embodiments of outer catheter 12, second lumen 22 is closed at its distal end. When stylet 26 is fully inserted into second lumen 22, the distal end of stylet 26 makes contact with this closed distal end of second lumen 22, thereby forcing outer catheter 12 forward along the same path being taken by stylet 26.

In other embodiments of outer catheter 12, second lumen 22 extends from second opening 24 to aperture 20. Stylet 26, in addition to providing rigidity to outer catheter 12 for its precise positioning within the brain, prevents brain tissue from entering second lumen 22 through aperture 20 during insertion. Stylet 26 is sized so as to not extend through aperture 20 when inserted into second lumen 22 and may be provided with either a proximal portion having a diameter greater than the diameter of second opening 24 or an annular flange (not shown) circumscribing the shaft of the stylet. Further insertion of stylet 26 into second lumen 22 beyond the position of the wider proximal portion, flange, or handle 27 is thereby resisted, forcing outer catheter 12 forward in the direction being taken by stylet 26.

After outer catheter 12 is satisfactorily positioned within the patient's brain using stylet 26 and stylet 26 is withdrawn from second lumen 22, plug member 28 seen in FIG. 2 is inserted into second opening 24 to seal off second lumen 22, thereby blocking cerebral brain fluid or other liquid agents that may enter second lumen 22 from being discharged through second opening 24 and likewise preventing bacteria and other contaminants from entering second lumen 22 where they could migrate to and infect the brain. Plug member 28 has a tapered body with a proximal portion having a diameter greater than the diameter of second opening 24 so that plug member 28 can fit snugly and securely within second opening 24. Plug member 28 is formed from stainless steel or a hard plastic such as polycarbonate.

Outer catheter 1-2, as illustrated in FIG. 1, has a closed distal end 30 and a plurality of apertures 20 in communication with first lumen 16. Apertures 20 are positioned above distal end 30 and arranged along exterior 32, axially and radially spaced about central axis 34. Alternate embodiments can also include an aperture 20 at distal end 30.

Inner catheter 14 is preferably polyimide, polyimide-coated glass or other similar material. Inner catheter 14 is provided with passageway 36 which extends from mouth 37 at proximal end 38 to port 40. Passageway 36 has an inner diameter which may vary depending on the desired flow rate of fluid through inner catheter 14 but is preferably between about 25 microns and 0.5 millimeters. Port 40 is shown coaxial with passageway 36 but other embodiments of inner catheter 14 could have non-coaxial openings. Applicant notes that one such preferred catheter is disclosed in U.S. patent application Ser. No. 10/423,587 filed by Applicant on Apr. 25, 2003, the disclosure of which is incorporated by reference herein.

Figure 7:
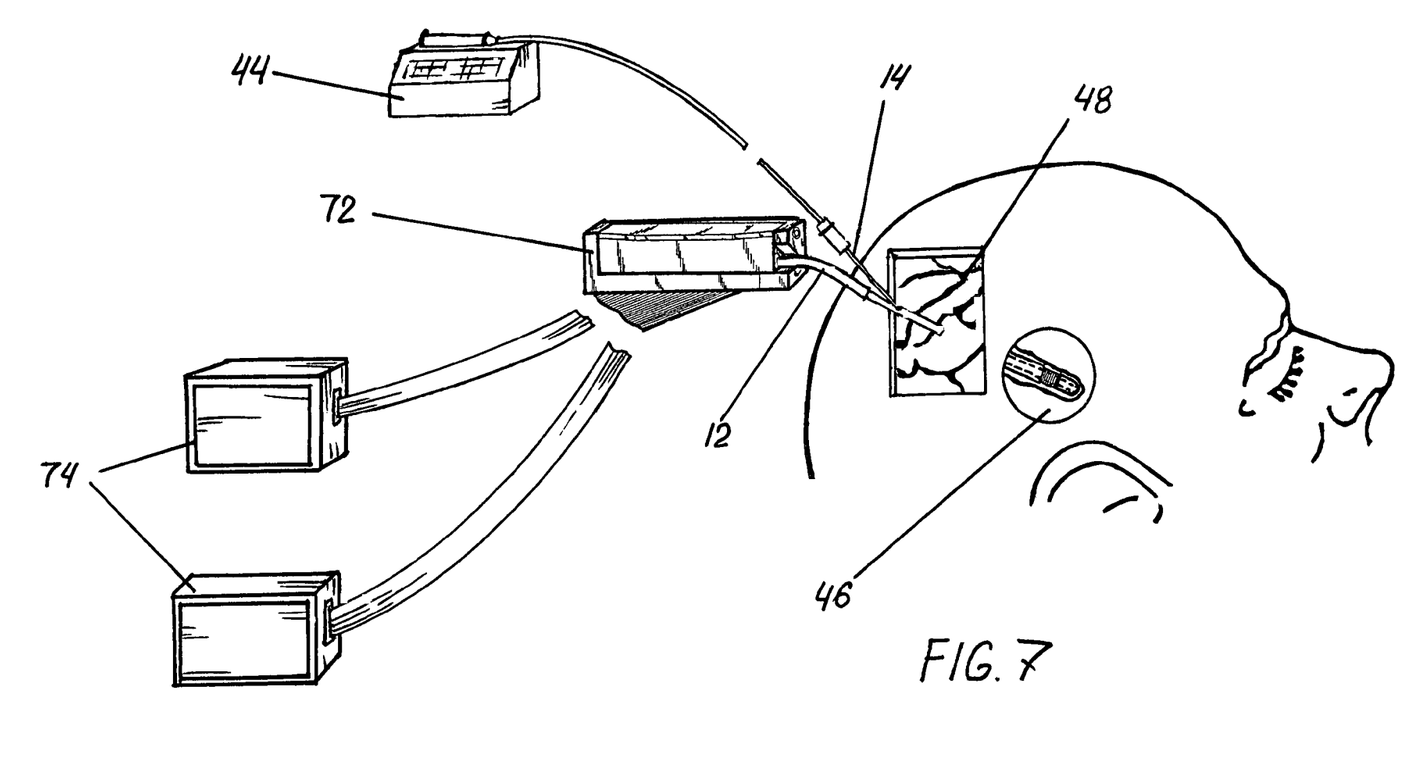
FIG. 7 is a schematic view illustrating the connection to external devices of an outer catheter and inner catheter in accordance with this invention and showing the catheters positioned within the brain.

Proximal end 38 of inner catheter 14 is provided with a tapered fitting 42, preferably a male luer conical fitting, to enable inner catheter 14, as seen in FIG. 7, to form a detachable air-tight joint with tubing or some other conduit having a female luer connector. In this manner, inner catheter 14 is operatively connected by the tubing to an external instrument such as pumping equipment 44. One skilled in the art will recognize that inner catheter 14 could also be connected to internal instrumentation having pumping capability. Such equipment allows fluids to be transferred to or from tissue region 46 of the brain 48 through port 40. Drugs may then be administered to tissue region 46, cerebral spinal fluid may be withdrawn, or both.

Inner catheter 14 of catheter assembly 10 is preferably provided with a micro-dialysis membrane 50 adjacent to port 40. After positioning outer catheter 12 in a targeted region of the brain, inner catheter 14 is inserted into first lumen 16 through first opening 18 so that apertures 20 of outer catheter 12 allow cerebral spinal fluid (CSF) to reach membrane 50. CSF moves through membrane 50 and is transferred through passageway 36 to external receptacles or analysis devices via pumping equipment.

Figure 6:
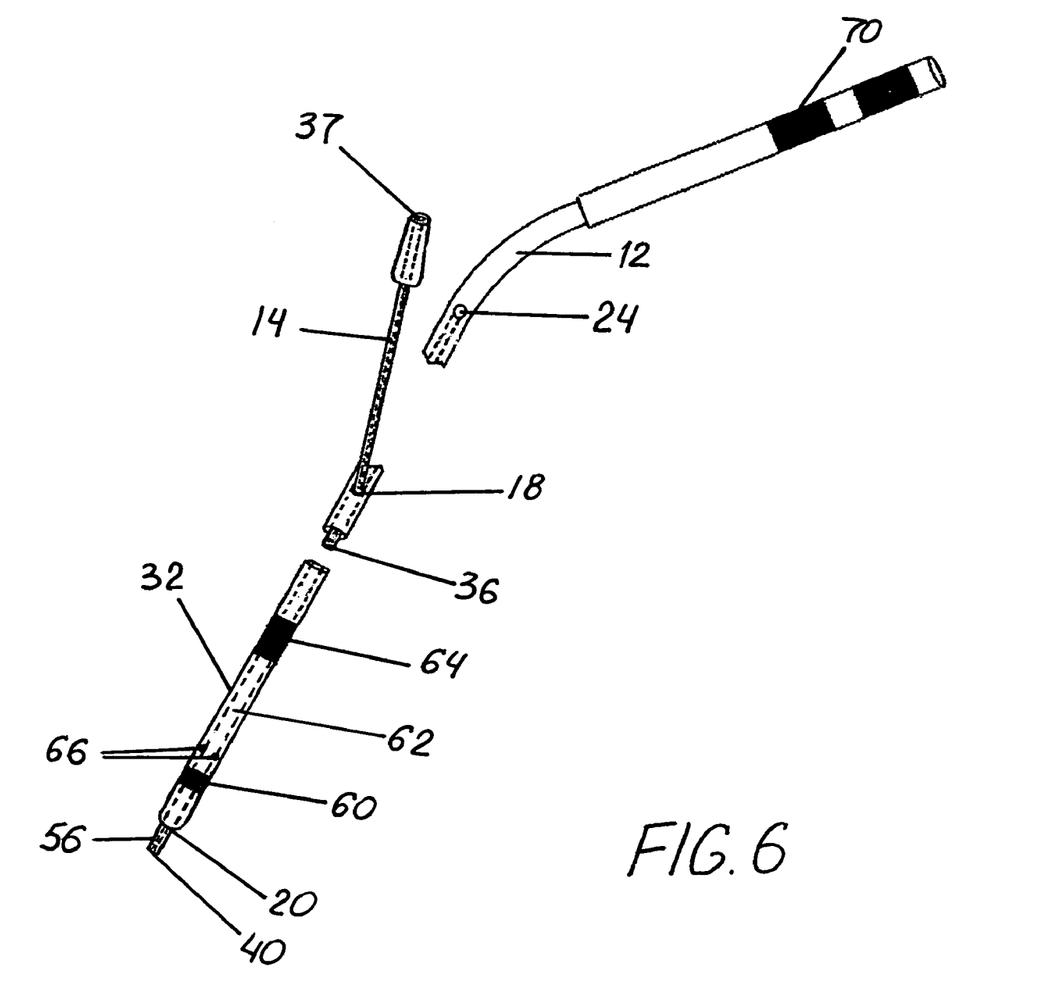
FIG. 6 is a perspective view of another preferred outer catheter receiving an inner catheter with cut-away sections to reveal and dashed lines to represent otherwise unseen internal features in accordance with this invention.

As seen in FIGS. 1 and 6, first and second openings 18, 24 are distal to proximal portion 52. Proximal portion 52 abuts the proximal end of outer catheter 12. First opening 18 is preferably 4 inches distal from second opening 24. Outer catheter 12 is sufficiently flexible to allow outer catheter 12 to be selectively bent so that either opening 18, 24 can be brought into coaxial alignment with distal end 30. In this manner, stylet 26 can be easily inserted into second opening 24 by axially aligning second lumen 22. Likewise, after precisely positioning outer catheter 12 in the brain using the stylet, inner catheter 14 can be more conveniently received within first lumen 16 by bending outer catheter 12 proximal to first opening 18.

Micro-dialysis is most effective over a short distance. An outer catheter 12 is therefore desirable that offers one lumen 16 for guiding an inner catheter 14 to a tissue region within a targeted area of the brain that is shorter than and distinct from the lumen 22 used with a stylet 26 to insert the outer catheter 12 into that targeted area.

Figure 4:
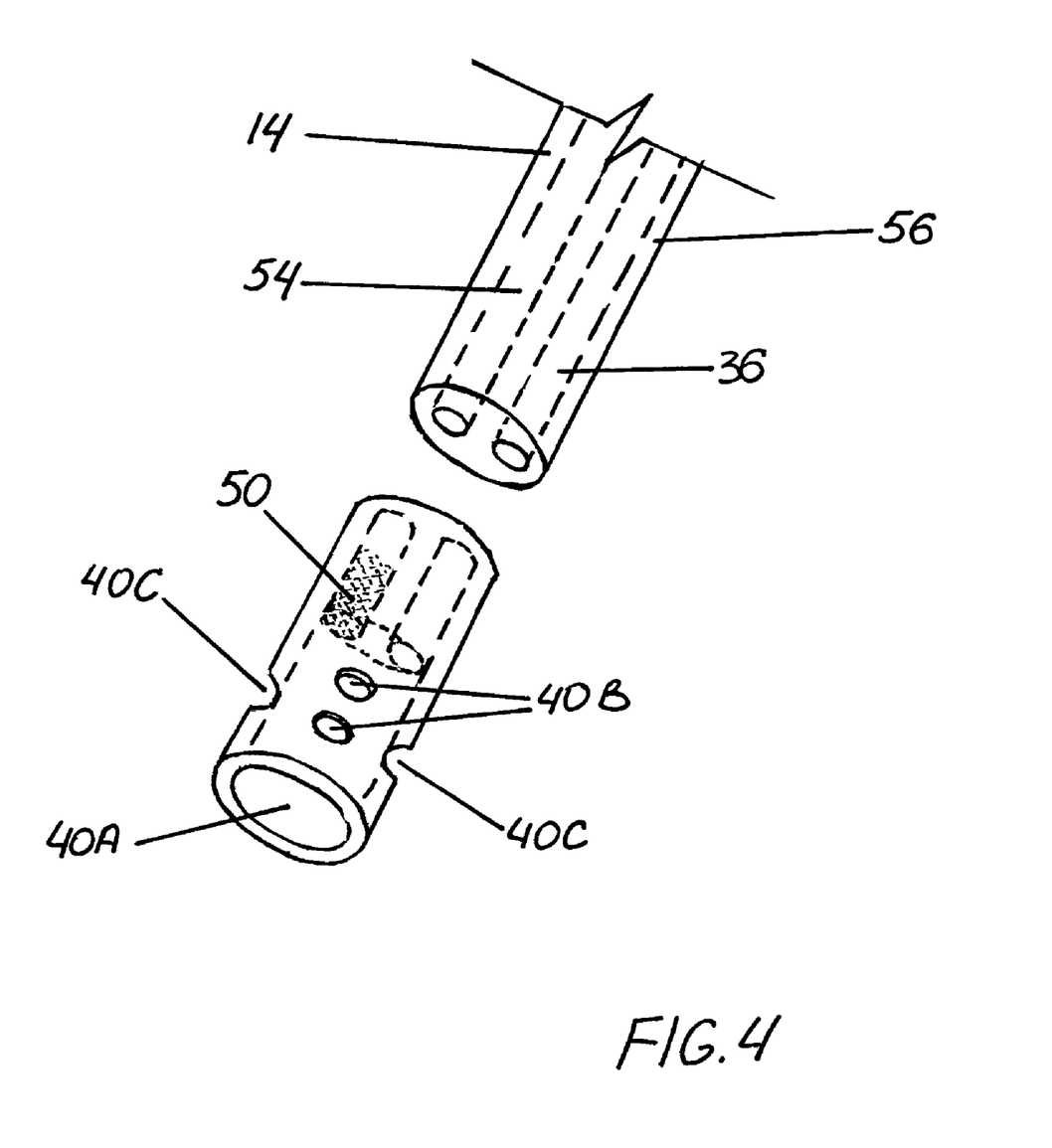
FIG. 4 is an enlarged perspective view of the distal end of another preferred inner catheter in accordance with this invention with cut-away section to reveal and dashed lines to represent otherwise unseen internal features.

One embodiment of an inner catheter 14 having a micro-dialysis membrane 50 is illustrated in FIG. 4. Inner catheter 14 is provided with first passageway 36 and an adjacent second passageway 54. Inner catheter 14 is shown with a plurality of ports 40 in fluid communication with the distal ends 56, 58 of each passageway 36, 54. Port 40A is coaxial with passageways 36, 54. Ports 40B are spaced axially and ports 40C are spaced radially along the exterior of the distal portion 56 of inner catheter 14. Membrane 50 is securely mounted at distal end 58 of second passageway 54. A liquid agent such as a drug can be inserted into a certain tissue region of the brain through first passageway 36 while CSF can be withdrawn from the same tissue region, passing over membrane 50 and through second passageway 54.

Figure 5:
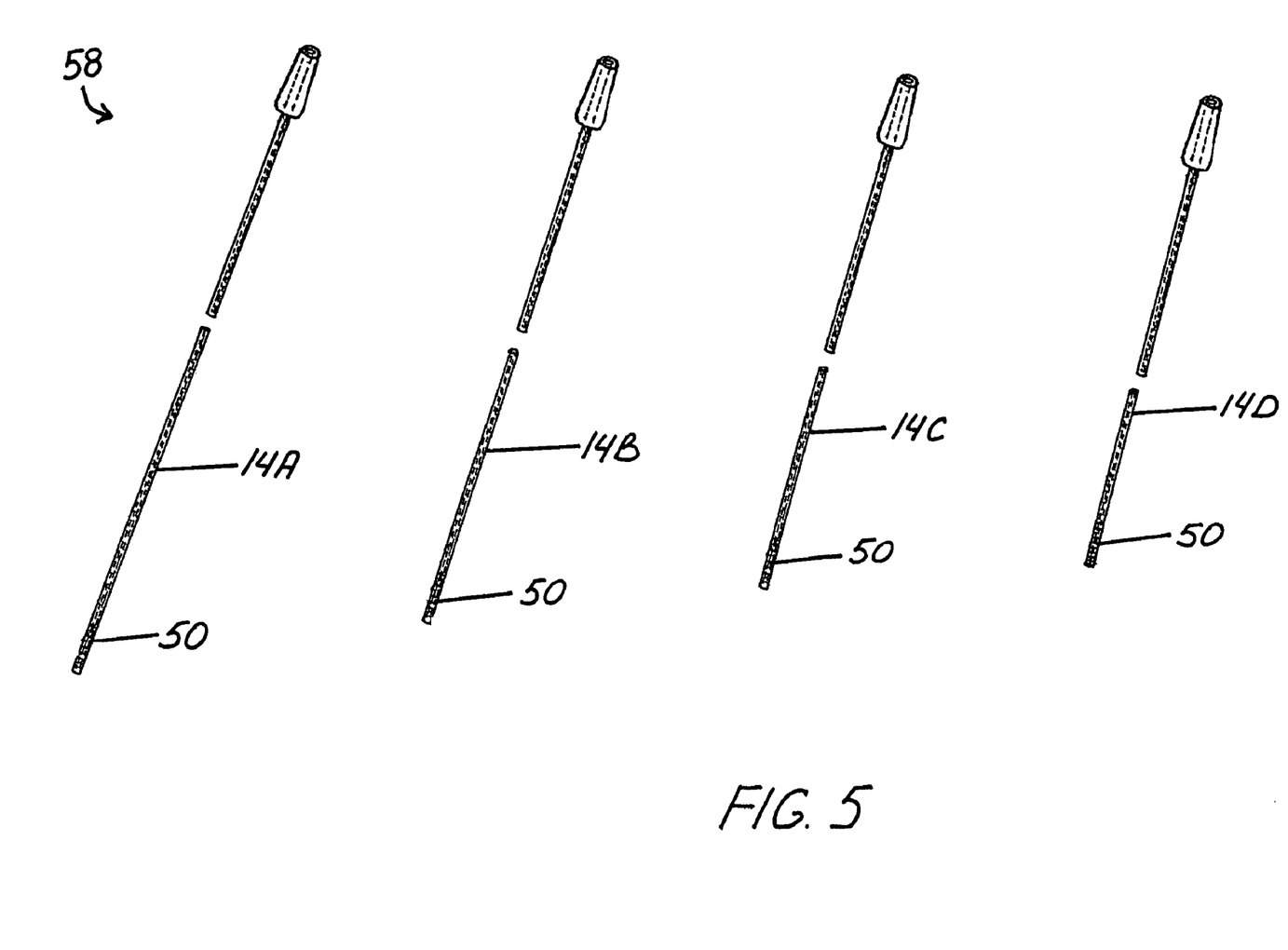
FIG. 5 is a perspective view of a plurality of alternate inner catheters in accordance with this invention, each having a different length, with cut-away sections to reveal and dashed lines to represent otherwise unseen internal features.

FIG. 5 depicts a set 58 of four inner catheters 14A-14D, each catheter having a different length. Set 58 is preferably used with an outer catheter 12 having an open distal end 30 such that at least one aperture 20 is coaxial with first lumen 16. In this embodiment, after inserting outer catheter 12 into the patient's brain, a first inner catheter 14A of a specific length is selected to treat a desired tissue region at a known location beyond outer catheter 12 by extending the inner catheter through aperture 20. After treatment at that location, first inner catheter 14A can be removed and a second inner catheter 14B of a different length can be inserted into the patient's brain to treat a different desired tissue region. For instance, an inner catheter 14 which extends 0.5 cm beyond outer catheter 12 may be used to treat the tissue region 0.5 cm beyond outer catheter 12 and then removed from first lumen 16 before another inner catheter 14 which extends 2.0 cm beyond distal end 30 of outer catheter 12 is inserted through first lumen 16 and used to treat the tissue region 2.0 cm beyond outer catheter 12.

The set 58 of inner catheters 14 can be any number and is provided as a catheter assembly with outer catheter 12 so that a physician can select a specific inner catheter 14 to treat a desired tissue region. The inner catheters 14 are preferably micro-dialysis catheters to allow for the withdrawal and subsequent analysis of CSF at different tissue regions without requiring multiple insertions through the intervening brain tissue.

Outer catheter 12 also includes elements 60 secured to distal portion 62. Elements 60 provide for monitoring of brain activity, for stimulating brain tissue or for serving as a location beacon to aid in determining the precise position of distal portion 62 within the brain. Elements 60 communicate with external monitoring and control equipment during treatment of the patient. Such communication can be by way of electrical, optical and/or radio-frequency transmission.

Elements 60 can take the form of contacts 64, as illustrated in FIGS. 1, 6 and 7. Contacts 64 comprise devices such as electrodes designed to monitor brain activity in tissue region 46 through the sensing of electrical and/or electrochemical changes within the brain or to provide electrical stimulation to specific areas of the brain. Electrodes serving as contacts 64 are preferably constructed from platinum, platinum-iridium or other bio-compatible conductive material. Electrodes can be macro-contacts that circumscribe or band outer catheter 12 or micro-contacts 66 capable of measuring electrical changes at the level of a single neuron.

Elements 60 can also can take the form of sensors designed to monitor brain activity within select tissue regions through the sensing of electrical, electrochemical, chemical, temperature or pressure changes within the brain. Sensors can be electrochemical and optical transducers designed to measure chemical, pressure, temperature, cerebral blood flow and other physiological changes in the brain. Such devices are known in the art and are preferably less than about 2 millimeters long.

Contacts 64 are preferably connected by leads 68 (seen in FIG. 3 running alongside first and second lumens 16, 22) to proximal-contacts 70. Leads 68 can be in the form of electrical wiring or a fiber-optic bundle. Proximal-contacts 70 are mounted along proximal portion 52 as shown in FIGS. 1, 6 and 7. Brain activity sensed by contacts 64 is transmitted to an external connector 72 through proximal-contacts 70 and then to a computer or similar instrument 74 having a conventional output display and monitor with a suitable power source where such activity can be recorded and/or analyzed. During insertion of outer catheter 12 into the brain, proximal-contacts 70 remain outside of the patient and allow for connection to monitoring equipment such as instrument 74. Proximal-contacts 70 are preferably formed from stainless steel or similar alloys or materials that are non-corrosive conductors and that can endure sterilization.

Element 60 can also take the form of a location marker 76 as seen in FIGS. 1 and 6. Location marker 76 is preferably a structure comprised of a non-ferrous material known in the art such as gold or tungsten that has an image signal intensity suitable for proton magnetic resonance imaging (MRI) with most commercial machines and is also sufficiently x-ray opaque for satisfactory imaging using computed tomographic scanning (CT) or on X-ray. Location marker 76 can also be comprised of a sensor capable of measuring voltages induced by a transmitted magnetic field that can be used to identify the position and orientation of the sensor within that field.

Elements 60 may be positioned on both the distal and proximal sides of apertures 20 along distal portion 62 as illustrated in FIG. 1. This configuration allows for monitoring of the tissue region of the brain that is being treated simultaneously with drugs or having CSF withdrawn. Micro-contacts 66 can be spaced axially along distal portion 62 as illustrated in FIG. 1 or spaced radially around outer catheter 12 as shown in FIG. 6.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention of claimed is:

1. A catheter assembly for intracranial treatment of a patient comprising:
an outer catheter having a proximal portion, a first lumen in communication with respect to a first opening and at least one aperture, and a second lumen in communication with respect to a second opening, each lumen having a channel with a substantially circular cross-section and the first and second openings being distal to the proximal portion; and
an inner catheter sized to be slidably, removably received coaxially within the first lumen and including at least one passageway and at least one port in communication with respect to the passageway for transferring at least one fluid with a tissue region of the brain of the patient.

2. The catheter assembly of claim 1 further comprising a rigid stylet and a plug member, the stylet being sized to be received within the second lumen whereby the stylet can be positioned within the second lumen for insertion of the outer catheter into the brain, and the plug member being adapted to snugly engage the second opening whereby the plug member can close off the second lumen following insertion of the outer catheter and the removal of the stylet.

3. The catheter assembly of claim 2 wherein the second lumen is in communication with respect to the aperture.

4. The catheter assembly of claim 2 wherein the second lumen is open only at the second opening.

5. The catheter assembly of claim 1 wherein the outer catheter has a closed distal end and an exterior, the aperture being spaced from the distal end along the exterior.

6. The catheter assembly of claim 5 wherein the outer catheter has an axis and at least first and second apertures in communication with respect to the first lumen, the first and second apertures being spaced axially along the exterior.

7. The catheter assembly of claim 5 wherein the outer catheter has an axis and at least first and second apertures in communication with respect to the first lumen, the first and second apertures being spaced radially about the axis along the exterior.

8. The catheter assembly of claim 5 wherein the inner catheter is a micro-dialysis catheter having a dialysis membrane at the port, the membrane being adapted to receive cerebral spinal fluid withdrawn from the tissue region through the aperture.

9. The catheter assembly of claim 8 wherein the inner catheter includes at least first and second passageways in communication with respect to the port, the second passageway including the dialysis membrane, whereby a liquid agent can be transferred to the tissue region through the first passageway and the cerebral spinal fluid can be withdrawn through the second passageway.

10. The catheter assembly of claim 1 wherein the aperture is at a distal end of the outer catheter.

11. The catheter assembly of claim 10 wherein the inner catheter is chosen from a plurality of inner catheters, each inner catheter having a different length for transferring the fluid with a select tissue region of the patient's brain and being sized to extend through the aperture when inserted into the outer catheter.

12. The catheter assembly of claim 11 further comprising at least first and second inner catheters chosen from the plurality of inner catheters, the first inner catheter having a first length for transferring the fluid with a first tissue region and the second inner catheter having a second length for transferring the fluid with a second tissue region, the second length being greater than the first length such that the second tissue region is at a greater distance distal from the aperture than the first tissue region.

13. The catheter assembly of claim 12 wherein each inner catheter is a micro-dialysis catheter having a dialysis membrane adapted to receive cerebral spinal fluid at the port.

14. The catheter assembly of claim 1 wherein the outer catheter further includes an axis and a distal end, the outer catheter being flexibly deformable such that the outer catheter can be selectively configured to form a bend proximal to one of the openings to position that opening in axial alignment with the distal end.

15. The catheter assembly of claim 1 wherein the outer catheter further includes a distal portion having at least one element.

16. The catheter assembly of claim 15 wherein the element is a contact that monitors brain activity.

17. The catheter assembly of claim 16 wherein the contact monitors electrical activity within the brain.

18. The catheter assembly of claim 16 wherein the contact is a micro-contact.

19. The catheter assembly of claim 15 wherein the element is a location marker to identify the position of the outer catheter when inserted within the brain.

20. The catheter assembly of claim 15 wherein the outer catheter has at least two elements spaced along the distal portion.

21. The catheter assembly of claim 20 each element is mounted proximal to a distal end of the outer catheter upon an exterior surface of the distal portion.

22. The catheter assembly of claim 15 wherein the proximal portion includes at least one proximal-contact, the proximal-contact conductively connected with at least one element.

23. A depth probe for intracranial treatment of a patient comprising:

a body extending from a proximal end to a distal end, the body having first and second openings, an axis and at least one aperture;

a first lumen defined by the body in communication with respect to the first opening and the aperture, the body being flexibly deformable such that the body can be selectively configured to form a bend proximal to the first opening to position the first lumen such that the first opening is in axial alignment with the distal end, the first lumen being sized to slidably, removably receive coaxially an inner catheter adapted to transfer fluids with a tissue region of the brain of the patient and having a channel with a substantially circular cross-section;

a second lumen defined by the body in communication with respect to the second opening, the second lumen being sized to receive a stylet adapted to facilitate insertion of a distal portion of the body into the tissue region and having a channel with a substantially circular cross-section; and a proximal portion at the proximal end, the openings being distal to the proximal portion and substantially proximally spaced from the distal portion.

24. The depth probe of claim 23 wherein the second opening is sized to receive and snugly engage a plug member such that the second lumen can be closed off by the plug member.

25. The depth probe of claim 23 wherein the body has an exterior and an axis and includes at least first and second apertures in communication with respect to the first lumen, the first and second apertures being spaced axially along the exterior.

26. The depth probe of claim 23 wherein the body has an exterior and an axis and includes at least first and second apertures in communication with respect to the first lumen, the first and second apertures being spaced radially about the axis along the exterior.

27. The depth probe of claim 23 further comprising a distal portion at the distal end, the openings being proximal to the distal portion, and the distal portion having at least one element.

28. The depth probe of claim 27 wherein the element is a contact that monitors brain activity within the tissue region.

29. The depth probe of claim 27 wherein the element is a micro-contact.

30. The depth probe of claim 27 wherein the element is a location marker to identify the position of the distal portion when the body is inserted within the brain.

31. The depth probe of claim 27 further comprising at least two elements spaced along the distal portion.

* * * * *